United States Patent [19]

Wichmann

[11] Patent Number: 4,746,613
[45] Date of Patent: May 24, 1988

[54] POULTRY DISEASES BACTERIN PREPARATION

[76] Inventor: Robert W. Wichmann, 21 College Park, Davis, Calif. 95616

[21] Appl. No.: 585,519

[22] Filed: Mar. 2, 1984

[51] Int. Cl.$^4$ .................. C12N 1/20; A61K 39/102
[52] U.S. Cl. ................................. 435/253; 424/93
[58] Field of Search ............ 435/240, 241, 253, 68, 435/261, 240.1; 424/88, 92, 93; 260/112 R; 530/350

[56] References Cited

U.S. PATENT DOCUMENTS

| | | | |
|---|---|---|---|
| 3,501,770 | 3/1970 | Gale et al. | 424/92 |
| 3,876,763 | 4/1975 | Yoshikazu et al. | 424/89 |
| 4,136,169 | 1/1976 | Rebers et al. | 424/92 |

OTHER PUBLICATIONS

Rimler et al. "Lysates of Turkey Grown *Pasteurella multocida*: "Profection against Homologous and Meterologous Serotype Challenge Exposures" Am. J. Vet. Res. 42, pp. 2117–2121, Dec. 1981.

Seeley et al., "Cultivation of Viruses in Tissue Culture" *Microbes in Action* (2nd ed.) 1972 (W. H. Freeman and Company) pp. 123–124.

Chemical Abstract No. 138556v; Matsumoto et al., "A Broth Bacterin against Infectious Coryza: Immunogenicity of Various Preparations", vol. 74, 1971; p. 318.

*Primary Examiner*—Elizabeth Weimar
*Attorney, Agent, or Firm*—Mark C. Jacobs

[57] ABSTRACT

A process for the propagation of bacteria in a tissue culture system and the preparation of a bacterin therefrom which bacterin has the capability of protecting fowl not only against homologous serotypes of the same organism, but also against heterologous serotypes of the same organism.

8 Claims, No Drawings

POULTRY DISEASES BACTERIN PREPARATION

BACKGROUND OF THE INVENTION

It has been known since the 1950s that infectious diseases of poultry such as infectious Corzya of chickens or Fowl Cholera of chickens or turkeys are caused by specific bacterial species. Infections Corzya is caused by the organism *Hemophilus gallinarum* (paragallinarum) and Fowl Cholera is caused by *Pasterurella multocida.*

It has also been known for some time that there are a number of different serotypes of these bacteria each of which is capable of causing nearly identical disease syndromes. Birds which have been infected naturally or artificially, i.e. by innoculation, with one serotype will, upon recovery, be resistant to disease if exposed to different serotypes of the same bacterial species. For instance, if a chicken is infected with *Hemophilus gallinarum* serotype A and following recovery is exposed to serotypes B or C it will be resistant to the second exposure. Similarly if a chicken or turkey has been exposed to *Pasterurella multocida,* Type 1, and recovers from the disease it will be resistant to subsequent exposure to types 3, 4, etc. This, of course, presumes that the bird survives the first onset of the disease.

For many years killed cultures of these bacteria (bacterins), which had been grown on various artificial media, have been used to attempt to prevent the disease caused by these organisms. Unfortunately, however, contrary results have arisen. Thus if a chicken is vaccinated with a bacterin prepared from *Hemophilus gellinarum* serotype A it will not be protected against exposure to serotypes B or C. Similarly fowl cholera bacterins prepared from type 1 *Pasteurella multocida* will not protect birds exposed to other types of Pasteurella.

It has been shown that bacterins prepared from organs such as livers that have been removed from turkeys that died of fowl cholera can be used to prepare a bacterin which is capable of protecting turkeys that have been vaccinated with this bacterin against exposure to heterologous types of *Pasteurella multocide* bacteria.

While such a finding is of academic interest it is not a practical procedure for commercial production of a bacterin.

DESCRIPTION OF KNOWN PRIOR ART

| U.S. Pat. No. | |
|---|---|
| 3,534,136 | Dunlop et al |
| 3,553,312 | Delgudo |
| 3,769,415 | Fenje |
| 4,210,719 | Tolbert et al |
| 4,211,843 | Dubreuil |

"Lysates of Turkey-Grown Pasteurella Multocida: Partial Solubilization of the Cross-Protection Factor" Am J. Vet. Res. October 82, P. 1781 et seq "Cultivation and Modification of the Avian Infectious Synovitis Agent in Tissue Culture", Wichmann et al, *Avian Diseases* Vol. 4 #2, May 1960

SUMMARY OF THE INVENTION

The instant procedure pertains to a process for procuring bacterins that are less monospecific than those of the prior art with respect to homologous and heterologous serotypes of a bacteria.

The process includes the following steps:
1. Utilize a standard tissue culture with no antibiotic added.
2. Introduce a supplementary serum as part of the growing medium. examples being horse serum, fetal calf serum, etc.
3. Introduce tissue such as chicken embryo, turkey embryo and the like, preferably in fragments rather than as individual cells.
4. Add the bacteria such as hemophillus, pasteurella or some other type.
5. Incubate
6. Stir during incubation to maintain suspension as by the use of magnetic stiring.
7. After growth has taken place, use a standard inactivation procedure to kill the bacteria and then a standard harvest method.
8. Use the collective bacteria now killed to prepare the bacterin.

It is a primary object of this invention to provide a process for preparing bacterins (killed culture bacteria) to immunize fowl against the various heterologous as well as homologous types of a bacteria.

It is another object to provide a method of immunizing chickens and turkeys against the several different types of *Hemophillus galliarum* and *Pasteurella multocida* bacteria.

Yet another object is to provide a process for immunizing birds against the several types of Fowl cholera.

A further object is to provide a process for preparing bacterins using a tissue culture medium.

Other objects of the invention will be part be obvious and will in part appear hereinafter.

The invention accordingly comprises the several steps and the relation and order of one or more of such steps with respect to each of the others and the product possessing the features, properties and the relation of elements which are exemplified in the following detailed disclosure, and the scope of which will be indicated in the claims.

For a fuller understanding of the nature and objects of the invention, reference should be had to the following detailed description of the invention.

DESCRIPTION OF THE PREFERRED EMBODIMENT

The current invention described a procedure for an in vivo type of growth of bacteria from which a bacterin can be prepared. Such a bacterin will provide complete protection against exposure to homologous serotypes and a statistically significant protection against heterologous exposure. A comparison chart set forth below will recite the increased protection against heterologous bacterin.

Several methods may be employed for producing bacterins in tissue cultures. In the following description the methods disclosed are for the purpose of illustrating the preparation bacterin since it will be within the skill of the microbiological art to employ other selective techniques within the parameters of this disclosure and the appended claims, to obtain similar results.

TISSUE CULTURE SELECTION

The first step for producing animal bacterins according to this invention is to select a tissue culture system and a source of tissues which will support the growth of the bacteria one wishes to grow. The tissues most desirable will be from the species of animal in which the bacterin will be used. Embryonic tissues obtained from embryonated eggs have proven satisfactory. Both chicken eggs and turkey eggs have been used. No reason is seen why duck and other fowl eggs would not yield similar results.

The age of the embryo appears to have little effect on the growth of the bacteria since chicken embryos from six (6) to twelve (12) days old have been satisfactorily used. There is a cost advantage to using the older embryos since fewer embryos are required due to size difference.

The tissue culture fluids used to sustain the embryos are many in number. Commercial media such as M199, MEM and L-15 have been used with equal success. Tryptose phospate broth has been shown to improve bacterial yields when incorporated in the tissue culture medium in concentrations ranging from two (2) to ten (10) percent and as such this optional ingredient's usage is recommended. Animal serum is an important addition for maximum yields of bacteria. Fetal bovine serum, horse serum and calf serum have all been used satisfactorily. Concentration of serum can range from two (2) to ten (10) percent of the final volume, but two (2) percent concentrations have been adequate. Sodium bicarbonate is a useful addition in low concentrations to raise the pH and buffers such as Tris are also useful to control pH. The pH of the solution should preferrably be about 7.4 at commencement but a range from 7.6 to 6.7 has been found satisfactory.

INACTIVATION

Inactivation of the bacteria prior to preparation of a bacterin is necessary. Any generally used inactivating material can be used, but the preferred reagent is binary ethylenimine. The use of an adjuvant is recommended to produce satisfactory bacterins. While the choice may vary with the bacterin, aluminum hydroxide gel or mineral oil emulsions have been found effective, on a generalized basis, among others.

A preferred process for preparing fowl bacterin according to this invention comprises the steps of:

(a) inoculating a tissue culture composed of embryonic tissue with bacteria;

(b) incubating the infected composition to produce a fluid portion containing large numbers of organisms of a type which would be recovered from a naturally infected fowl;

(c) recovering said bacteria from the culture by coarse filtration or centrifugation;

(d) inactivating the bacteria;

(e) preparing a bacterin from the inactivated bacteria by adding adjuvant to the killed culture or incorporating the killed culture into an adjuvant.

The methodology of this invention will be discussed with respect to the preparation of two different bacterins. The first of which is to fight infectious Coryza of chickens while the second pertains to Fowl Cholera.

Turning now to the individual steps involved in the total process for preparing bacterins, the first of which is the step of inoculating a tissue culture with bacteria.

In general, the philosophy of the art has been to avoid the use of live tissue culture for the growth of bacteria because it was cheaper and easier to use solid agar base or broth type media and because of the use of steam sterilization of media used there was little or no need for antibiotics during the inoculation step. My investigation shows that just about any tissue culture media and any type of serum supplement which is capable of sustaining the growth of tissues will be capable of allowing the bacteria to grow to concentrations and to be of a type to provide a good bacterin end product, ie. one that will provide a high degree of cross-protection when challenged with various serotypes. By using a tissue culture medium, it is felt that there is a closer approximation to the living conditions of a true host animal for the growth of the bacteria for the bacterin.

To tissue culture of the animal species to be protected by the bacterin, is added a serum, such as fetal calf serum, horse serum and the like, all of which are readily available in the marketplace from such vendors as KC Biologicals, GIBCO and others, and which sera are employed here as a growth medium supplement. Thus as the primary growth medium. mention can be made of chick embryo tissue, turkey embryo tissue etc. Preferably the tissue chosen, here fowl, should be embryo tissue, and not that of a grown chicken etc.

It is further preferred to use tissue fragments, rather than individual cells because there is less opportunity for contamination. This culture, comprised of tissue fragments and serum is added MEM, which is minimum essential medium which comprises approximately eighty-eight percent (88%) of the solution. The solution should preferably be buffered, to a pH of about 7.2 to about 7.4 using tryptose phosphate broth or some other buffering agent such as sodium bicarbonate in order to maximize the yield.

The operating temperature can range from 30° C. up to about 39° C., with about 37 degrees giving ease of operation.

The second step calls for the incubation of the tissue culture, a technique that is quite conventional and which need not be discussed in detail. The incubation is carried out with stirring to maintain a suspension. The incubation is carried out using the species and one of the serotypes of the bacteria desired for the bacterin. Of such bacteria, mention can be made of Pasteurella, *Hemophilus gallinarum,* Corynebacteria, *Escherichia coli* among others. The incubation is permitted to proceed until adequate growth has transpired, as measured by optical density.

At this point, binary ethylenimine, formalin or some other conventional agent such as thimerasol, is used to inactivate the bacteria. Coarse filtration or centrifugation is carried out to separate the bacterial cells from the tissue fragments or culture fluids. A conventional harvesting procedure is practiced.

The medicament is prepared using the bacterin obtained from the generalized procedure just described by adding an adjuvant to the killed bacteria, or by incorporating the bacteria into an adjuvant. An emulsion can be prepared if desired, using commercially available emulsifying agents, such as members of the Tween® or Span® family, among others.

At times it may be desirable to prepare a smaller quantity of culture which can then be used to inoculate a larger volume. Such a procedure maintains the bacterial agent in the log phase of growth which will generally shorten the incubation time required for maximum yields of bacteria.

Reference should now be made to the specific examples which further illustrate the preparation of cross-protection bacterins made in accordance with the instant invention, and the utilization thereof. As will be demonstrated, the results are superior to bacterins prepared using other techniques, due perhaps to the fact that the environment for growth bacteria which are incorporated into the bacterin more closely simulates the environment of bacteria that one would obtain from a naturally infected bird or animal.

EXAMPLE I

Infectious Coryza of Chickens

Eleven day old embryos are aseptically removed from the incubated eggs. These are minced with scissors or forced through a syringe which will fragment the embryo. These tissue are added at a rate of about one embryo per liter of tissue culture medium, which medium consists of medium 199 plus ten percent (10%) tryptose phosphate broth, plus 0.06% sodium bicarbonate, plus two percent (2%) horse serum.

The cell culture is incubated at 35° to 37° C. After a few hours of incubation the tissue culture is inoculated with *Hemophilus gallinarium,* either serotype A or B or C. Incubation is continued for twenty-four (24) hours at which time the cultures are removed from the incubator and thimerosal is added to a final concentration of 1:10.000.

After inactivation the cultures are passed through a stainless steel screen of sufficiently small mesh in order to remove the fragments of the embryonic tissue. A bacterin may be prepared by mixing equal volumes of fluids containing each serotype, which calls for addition of aluminum hydroxide gel to a final concentration of twenty percent (20%), however, since the purpose of this invention is to prepare a bacterin with only one serotype for the purpose of demonstrating cross protection against heterologous serotypes or if an autogenous bacterin is prepared for use of a specific form, then in such instance the aluminum hydroxide gel may be increased to twenty-five percent (25%).

At times it may be desirable to prepare a smaller quantity of culture which an then be used to inoculate a larger volume. Such a procedure maintains the bacterial agent in the log phase of growth which will generally shorten the incubation time required for maximum yields of bacteria.

The value of the bacterin was tested by conventional laboratory procedures in chickens.

EXAMPLE II

Tissue cultures are prepared as described in method one, however instead of inoculating these cultures with *Hemophilus gallinarum,* the cultures are inoculated with *Pasteurella multocida* which may be any one of several more common serotypes such as type I, III, or IV. Type II is not employed as it is a warm blooded animal disease. There are rare serotypes numbering up to about types 18 or 19. Incubation is continued for 18 to 24 hours until maximum growth of the bacteria is obtained. At this time the cultures are removed from the incubator and thimerosal is added to a concentration of 0.01%.

After inactivation the cultures are passed through a stainless steel screen of sufficiently small mesh so that the fragments of embryonic tissue are removed. The bacterial cultures are then centrifuged to separate the bacterial cells from the tissue culture fluids. The bacterial cells are then resuspended in a physiological saline solution which contains thimerosal at a concentration of 0.01%.

The final step in the preparation of the bacterin is to prepare a water in oil emulsion or a multiple emulsion. Both procedures utilize a highly refined mineral oil and the emulsifiers Arlacel 80 and Tween 80. The multiple emulsion results in a product which is less viscous and less irritating to the vaccinated animal. This procedure consists of first preparing a water-in-oil emulsion in which the aqueous suspension of bacterial cells is added to an equal volume of oil containing ten percent (10%) Arlacel 80 and homogenizing with a blender or homogenizer until an emulsion is formed and then adding this water in oil emulsion to equal parts of physiological saline containing two percent (2%) Tween 80 and blending this mixture until an oil in water emulsion is obtained. While monovalent bacterins are prepared by this procedure, in practice a blend of serotypes is used in the preparation of the final product to give the animal or fowl maximum cross protection against some of the rarer serotypes of *Pasteurella multocida.*

The following table is presented as an evaluation of a fowl cholera bacterin prepared in accordance with this invention to illustrate the protection available for heterologous challenge from several serotypes of the disease when the chickens are vaccinated with a bacterin made but from a single strain. See Table 1.

In the chart X73=Serotype 1, Pl059=Serotype 3 when 1x to 2x=number of inoculations of all birds in the group.

In tests against infectious coryza where birds were inoculated with the disease using conventional techniques, after having been pretreated with a bacterin from one type of the disease, said bacterin being prepared according to this invention, it was found that there was significant immunization protection against the other serotypes of this disease as well. See Tables 2, 3, & 4.

TABLE 1

EVALUATION OF A FOWL CHOLERA BACTERIN IN CHICKENS FOR PROTECTION AGAINST HETEROLOGOUS CHALLENGE

| No. Birds | Vaccine | Post challenge Mortality (Days)[a] | | | | | | | | | | | | | | Percent Mortality | Mean Day of Death |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | | |
| 10 | X-73 2x | | | | | | | | | | | | | | | 0 | |
| 10 | P-1059 2x | | | | | | | | 2(b) | | | | | | | 20 | 8 |
| 5 | X-73 1x | | | | | | | | | | | | 1(b) | | | 20 | 12 |
| 5 | P-1059 1x | | | | | | | | | | | | 1 | | | 20 | 13 |
| 15 | Non-Vac. | 3 | 4 | | | 1 | | 1 | | | | | 2(bb) | | | 73 | 4.3 |

[a]All birds challenged with Serotype 1 (X-73).
(b)Pasteurella not isolated from carcass.
(bb)Pasteurella not isolated from one of two carcasses.

TABLE 2

The Clinical Response of Vaccinated Chickens following Exposure to Serotype A, *Hemophilus gallinarum.*

| Treatment | Bird No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Trivalent Bacterin 1x | 116, 117, 118, 119, 125, 143 | | | | | | | NO CLINICAL SIGNS | | | | | | | |
| Trivalent Bacterin 2x | 160, 161, 162, 163, 164, 165 | | | | | | | NO CLINICAL SIGNS | | | | | | | |
| Monovalent Bacterin (serotype A) 1x | 179, 180, 181, 182, 183 | | | | | | | NO CLINICAL SIGNS | | | | | | | |
| Monovalent Bacterin (serotype A) 2x | 197, 198, 200, 228, 229 | | | | | | | NO CLINICAL SIGNS | | | | | | | |
| Non-vaccinated Controls | 105 | −A. | + | + | + | | | − | − | − | − | − | | | +L |
| | 106 | − | − | − | +B | | | +B,FSR | − | − | − | − | | | +B |
| | 107 | − | − | +R | +B,FS | | | FSL | FSL | +B,FSR | + | +FSL | | | +R |
| | 108 | − | − | − | +,FS | | | +B,FSR | +B | +B | − | − | | | − |
| | 109 | + | +B | +B | +B,FSL | | | +B,FS | +R,FSR | +R | + | + | | | +B |
| | 110 | + | + | + | + | | | − | − | − | − | − | | | +R |

A. − = No clinical signs
+ = Nasal exudate left nare; +R = nasal exudate right nare; +B = bilateral nasal exudate FSR or FSL = facial swelling right or left

TABLE 3

The Clinical Response of Vaccinated Chickens following Exposure to Serotype B, *Hemophilus gallinarum.*

| Treatment | Bird No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Trivalent Bacterin 1x | 148, 149, 150, 151, 152, 153 | | | | | | | NO CLINICAL SIGNS | | | | | | | |
| Trivalent Bacterin 2x | 166, 167, 168, 169, 170, 171 | | | | | | | NO CLINICAL SIGNS | | | | | | | |
| Monovalent Bacterin (serotype A) 1x | 185, 186, 187, 188, 190 | | | | | | | NO CLINICAL SIGNS | | | | | | | |
| Monovalent Bacterin (serotype A) 2x | 230, 231, 232, 233, 234, 235 | | | | | | | NO CLINICAL SIGNS | | | | | | | |
| Non-vaccinated Controls | 242 | +A. | + | +B | +B,FSB | | | +B | + | + | − | − | | | − |
| | 111 | − | − | +B | +B,FSB | | | + | + | +B | + | +R | | | +B |
| | 112 | + | + | + | +B,FSB | | | +B,FSL | − | − | − | − | | | − |
| | 113 | − | − | +R | +B,FSB | | | +B | − | − | − | − | | | − |
| | 114 | + | + | +R | +B | | | +B | + | + | + | − | | | +B |

A. − = No clinical signs
+ = Nasal exudate left nare; +R = nasal exudate right nare; +B = bilateral nasal exudate FSL or FSB = facial swelling left or bilateral

TABLE 4

The Clinical Response of Vaccinated Chickens following Exposure to Serotype C, *Hemophilus gallinarum.*

| Treatment | Bird No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Trivalent Bacterin 1x | 154, 155, 156 | | | | | | | NO CLINICAL SIGNS | | | | | | | |

TABLE 4-continued

The Clinical Response of Vaccinated Chickens following Exposure to Serotype C, *Hemophilus gallinarum.*

| Treatment | Bird No. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Trivalent Bacterin 2x | 157 158 159 172 173 174 175 176 177 | | | | | | NO CLINICAL SIGNS | | | | | | | | |
| Mono- valent Bacterin (serotype A) 1x | 191 | −A. | + | + | + | + | + | − | − | − | − | − | | | − |
| | 192 | − | − | − | − | − | − | − | − | − | − | − | | | − |
| | 193 | − | + | + | − | − | − | − | − | − | − | − | | | − |
| | 194 | − | + | + | − | − | − | − | − | − | − | − | | | − |
| | 195 | − | − | − | +R | +R | +R,FS | − | − | − | − | − | | | − |
| | 196 | − | − | + | + | − | − | − | − | − | − | − | | | − |
| Mono- valent Bacterin (serotype A) 2x | 236 | − | + | + | +,FSL | + | + | − | − | − | − | − | | | − |
| | 237 | − | − | − | − | − | + | + | +,FSL | − | − | − | | | − |
| | 238 | − | − | − | − | + | +B | +B,FSL | − | − | − | − | | | − |
| | 239 | − | − | − | − | − | − | − | | | | Cannibalized | | | |
| | 241 | − | + | − | − | − | − | − | − | − | − | − | | | − |
| Non- vaccinated Controls | 243 | − | − | − | − | − | − | − | − | − | − | − | | | − |
| | 244 | + | +B | +B | +L | + | + | + | + | + | + | + | | | − |
| | 245 | − | − | + | +,FSL | + | +B | − | − | − | − | − | | | − |
| | 246 | + | + | + | +,FSL | +B,FSB | +B,FSB | +B,FSB | +B | +B | +B | +B,FSL | | +B,FSR | +B,FSR |
| | 247 | − | − | + | + | +FS | +B,FSB | +B | +B | +B | +B | +B | | +B | +B |
| | 248 | − | + | + | + | +B | +B,FSL | +FSL | + | + | + | + | | | − |

A.— = No clinical signs
+ = Nasal exudate left nare; +R = nasal exudate right nare; +B = bilateral nasal exudate FSR or FSL = facial swelling right or left Since certain changes may be made in the above apparatus without departing from the scope of the invention herein involved, it is intended that all matter contained in the above description and shown in the accompanying drawings shall be interpreted as illustrative and not in a limiting sense.

I claim:

1. A method of preparing bacterins for the immunization of fowl which comprises:
   (a) inoculating an embryonic fowl tissue culture consisting essentially of fragmented embryo with a serotype of bacteria,
   (b) incubating said tissue culture to permit growth of said serotype of bacteria,
   (c) recovering the serotype of bacteria from the said tissue culture,
   (d) inactivating the said serotype of bacteria,
   (e) mixing the inactivated serotype of bacteria with an adjuvant.

2. The method of claim 1 wherein the recovery step comprises coarse filtration.

3. The method of claim 1 wherein the recovery step comprises centrifugation.

4. The method of claim 1 wherein the tissue of the tissue culture inoculated is chick embryo.

5. The method of claim 1 wherein the said bacterin is prepared by adding aluminum hydroxide as an adjuvant.

6. The method of claim 1 wherein the serotype of bacteria is *Pasteurella multocida* and the embryo used is chick embryo.

7. The method of claim 1 wherein the serotype of bacteria is *Hemophilus gallinarum* and the embryonic tissue is chick embryo.

8. The method of claim 1 wherein the serotype of bacteria is *Pasteurella multocida* and the embryo used is turkey embryo.

* * * * *